(12) United States Patent
Lai et al.

(10) Patent No.: US 7,859,677 B2
(45) Date of Patent: Dec. 28, 2010

(54) OPTICAL CALIBRATION SYSTEM AND METHOD

(75) Inventors: Ming Lai, Webster, NY (US); Lloyd G. Allred, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 404 days.

(21) Appl. No.: 11/610,059

(22) Filed: Dec. 13, 2006

(65) Prior Publication Data
US 2008/0144035 A1 Jun. 19, 2008

(51) Int. Cl.
*G01N 21/47* (2006.01)
(52) U.S. Cl. .................................. 356/446; 356/243.1
(58) Field of Classification Search ................ 356/124, 356/243.1, 446; 351/200
See application file for complete search history.

(56) References Cited

U.S. PATENT DOCUMENTS

| | | | | |
|---|---|---|---|---|
| 4,682,894 | A * | 7/1987 | Schmidt et al. ............. 356/614 |
| 5,512,965 | A | 4/1996 | Snook |
| 5,512,966 | A | 4/1996 | Snook |
| 5,735,283 | A | 4/1998 | Snook |
| 5,886,767 | A | 3/1999 | Snook |
| 5,909,270 | A | 6/1999 | Moser et al. |
| 6,193,371 | B1 | 2/2001 | Snook |
| 6,575,573 | B2 | 6/2003 | Lai et al. |
| 6,692,126 | B1 | 2/2004 | Xie et al. |
| 2002/0101567 | A1* | 8/2002 | Sumiya ...................... 351/206 |
| 2002/0171804 | A1 | 11/2002 | Rathjen |
| 2003/0112410 | A1* | 6/2003 | Altmann ..................... 351/212 |
| 2004/0008343 | A1* | 1/2004 | Pawluczyk et al. ....... 356/243.1 |
| 2004/0080759 | A1 | 4/2004 | Shaver |
| 2004/0169857 | A1* | 9/2004 | Acosta et al. ............... 356/328 |
| 2007/0019188 | A1* | 1/2007 | Nolot ....................... 356/243.4 |
| 2008/0285029 | A1* | 11/2008 | Benni et al. ................ 356/320 |

FOREIGN PATENT DOCUMENTS

EP 0317768 A1 5/1989

* cited by examiner

*Primary Examiner*—Kara E Geisel
(74) *Attorney, Agent, or Firm*—Jeffrey B. Powers

(57) ABSTRACT

An optical system calibration system and method particularly suited for calibrating the optical slit planes in an ophthalmic diagnostic instrument. The system includes an illumination source projector, an illumination image receiver, and a calibration component all having known relative positions, orientations and physical and optical characteristics. The calibration component includes at least two separated, diffusely reflecting surfaces. Images of an exemplary slit illumination pattern projected onto the calibration component and formed on the diffusely reflecting surfaces are detected by the image receiver such as a video camera. Based upon camera image coordinates and triangulation parameters of the projector, the receiver, and the calibration component, the slit image positions on the image detector plane can be calibrated to the axially displaced, diffusely reflecting calibration component surface positions.

34 Claims, 7 Drawing Sheets

OPTICAL CALIBRATION SYSTEM AND METHOD

CROSS REFERENCE TO RELATED APPLICATIONS

N/A.

FEDERALLY SPONSORED RESEARCH

N/A.

BACKGROUND OF THE INVENTION

1. Field of the Invention

Embodiments of the invention generally relate to an optical system calibration system and method. More particularly, embodiments of the invention are directed to a system and method for calibrating an ophthalmic diagnostic instrument. Most particularly, an optical slit plane calibration apparatus and method are disclosed.

2. Description of Related Art

Eye models provide a valuable tool for assessing the optical, physical and biophysical characteristics of human eyes and those of other species. In order to construct accurate eye models, the shapes and locations of the various ocular surfaces as well as their functions and effects need to be known with a high degree of precision. Alignment has always been a serious issue in creating eye models from image data. Misalignment errors directly result in errors in both estimates of optical power and details about the reconstructed ocular surfaces.

Bausch & Lomb Incorporated (Rochester, N.Y.) is an example of one company that has traditionally used a diagnostic slit beam to illuminate the eye. The slit beam is projected from about a 45 degree angle with respect to the instrument axis. A CCD camera is positioned along the axis. A subject's eye is aligned with the instrument axis and the subject's cornea is positioned at an imaging plane of the camera. The slit beam is scanned in a step-wise manner across the cornea for each eye measurement. The camera captures an image at each step of the slit beam position. By examining a series of these digital images of the slit beam illumination on various surfaces of the eye, three-dimensional models of the eye's surfaces can be obtained. In order to obtain accurate modeling results, it is desirable to obtain good characterization of the slit beam profile and accurate calibration of slit image displacement as measured on the camera detector. In particular, the relationship between the measured parameters and the physical displacement of the scattering surfaces of the eye that are intersected with the slit beam are determined at various locations along the slit beam optical path. The characterization and calibration just referred to will herein be referred to as slit plane calibration.

Slit plane calibration is typically performed with the use of an optical slit projection source, a camera/detector, and a test plate, having known position and orientation coordinates in a plane. The test plate has a scattering surface that is typically flat and painted black to reduce the amount of diffusely reflected light. This test plate is placed close to the imaging plane of the camera and the scattering surface is aligned normal to the instrument axis. The scattering surface is then positioned precisely at a number of axial positions and slit images are captured for the scan sequence at each axial position. Using triangulation techniques, one can analyze where the slit beam impinges on the test plate for a given calibration set-up and calibrate the slit beam width and optical path for that set-up from the known and measured data. This is repeated for additional set-ups to obtain full system calibration.

There are several drawbacks associated with the aforementioned calibration technique and apparatus. The precise placement of the test plates presents challenges in regard to mechanical alignment repeatability and mechanical alignment accuracy. Traditional alignment plates/fixtures can unknowingly be bent or otherwise deformed thus affecting alignment accuracy. The need for multiple physical alignment measurements and sets of images increases the opportunity for error. In addition, it is often necessary to position extra optical occluders along the path of the slit beam to reduce illumination intensity.

In view of the foregoing difficulties encountered with traditional mechanical alignment apparatus and techniques, the inventors have recognized a need for an apparatus and method that simplifies the calibration measurement, improves measurement accuracy and repeatability, is less time consuming and more technically efficient, is integratable with other diagnostic equipment, and offers other benefits and improvements over current apparatus and techniques that will be appreciated by persons skilled in the art.

SUMMARY

An embodiment of the invention is directed to an optical system calibration system. The calibration system includes an illumination projector (P) having an illumination projection axis lying in a plane. The projector is positioned at a selected reference location coordinate $(x_P, y_0, z_P)$ in the plane and the projection axis has a known projection direction in the plane. The system includes an illumination imager (R) having an imaging axis lying in the plane. The receiver is positioned at a known receiver location coordinate $(x_R, y_0, z_R)$ in the plane. The system further includes a calibration component (C) comprising at least a first at least partially diffusely reflecting surface disposed along the projection axis at a known first surface location coordinate $(x_{C1}, y_0, z_{C1})$ and a second at least partially diffusely reflecting surface disposed along the projection axis at a known second surface location coordinate $(x_{C2}, y_0, z_{C2})$ that is different than the first surface location coordinate. The system also includes a processing component operatively coupled to the system and adapted to determine a calibration indicia for the system. According to an aspect, the calibration component comprises at least a third at least partially diffusely reflecting surface disposed along the projection axis at a known third surface location coordinate that is different than the first and the second surface location coordinates. According to an aspect, one or more of the diffusely reflecting surfaces may also be optically transmissive to allow at least partial transmission of the illuminating light and certain diffusely reflected light, depending upon the calibration component geometry. According to an aspect, the calibration indicia describes a relationship between planar separation coordinate parameters $(\Delta x, \Delta y)$ of at least two different diffuse illumination images on a detector in the imager and an axial separation distance $(\Delta z)$ between the at least two respective diffusely reflecting surfaces of the calibration component.

Another embodiment of the invention is directed to method for calibrating an optical system. The method includes the steps of projecting an illumination pattern from a selected projection location, having a projection axis and known projection axis direction; illuminating, with the illumination pattern, a plurality of partially diffusing calibration component surfaces disposed along the projection axis at respective known calibration component surface locations; imaging the plurality of diffusely scattered illumination images from the plurality of diffusely reflecting surfaces of the calibration component on an image sensor positioned at a known imager location; and calibrating the optical system based upon the projector, imager, and calibration component surface location and direction parameters and sensor image parameters. According to an aspect, the relative position of either the projector or the camera can be changed along a line containing the known positions of the projector and camera. In this manner, the illumination pattern is scanned across the surface of the calibration component. Image edge and/or centroid coordinate mapping may not be linear for different scan positions, thus this calibration adjustment may be useful.

The system and method embodiments described herein may provide calibration data from a single set of images, may require only a single alignment, and may exhibit alignment accuracy that is independent of mechanical positioning variability of repeat measurements.

The system and method embodiments described herein are suitable for slit plane image calibration that is particularly useful for determining physical and optical parameters of an eye including, but not limited to, the cornea, the anterior chamber, the crystalline lens, and the retina.

In various aspects, the system and method embodiments can include the use and operation of an ophthalmic wavefront sensor for further determining physical and optical parameters of an eye.

The foregoing and other objects, features, and advantages of embodiments of the present invention will be apparent from the following detailed description of the embodiments, which make reference to the several drawing figures.

DETAILED DESCRIPTION OF THE INVENTION

Figure 1:
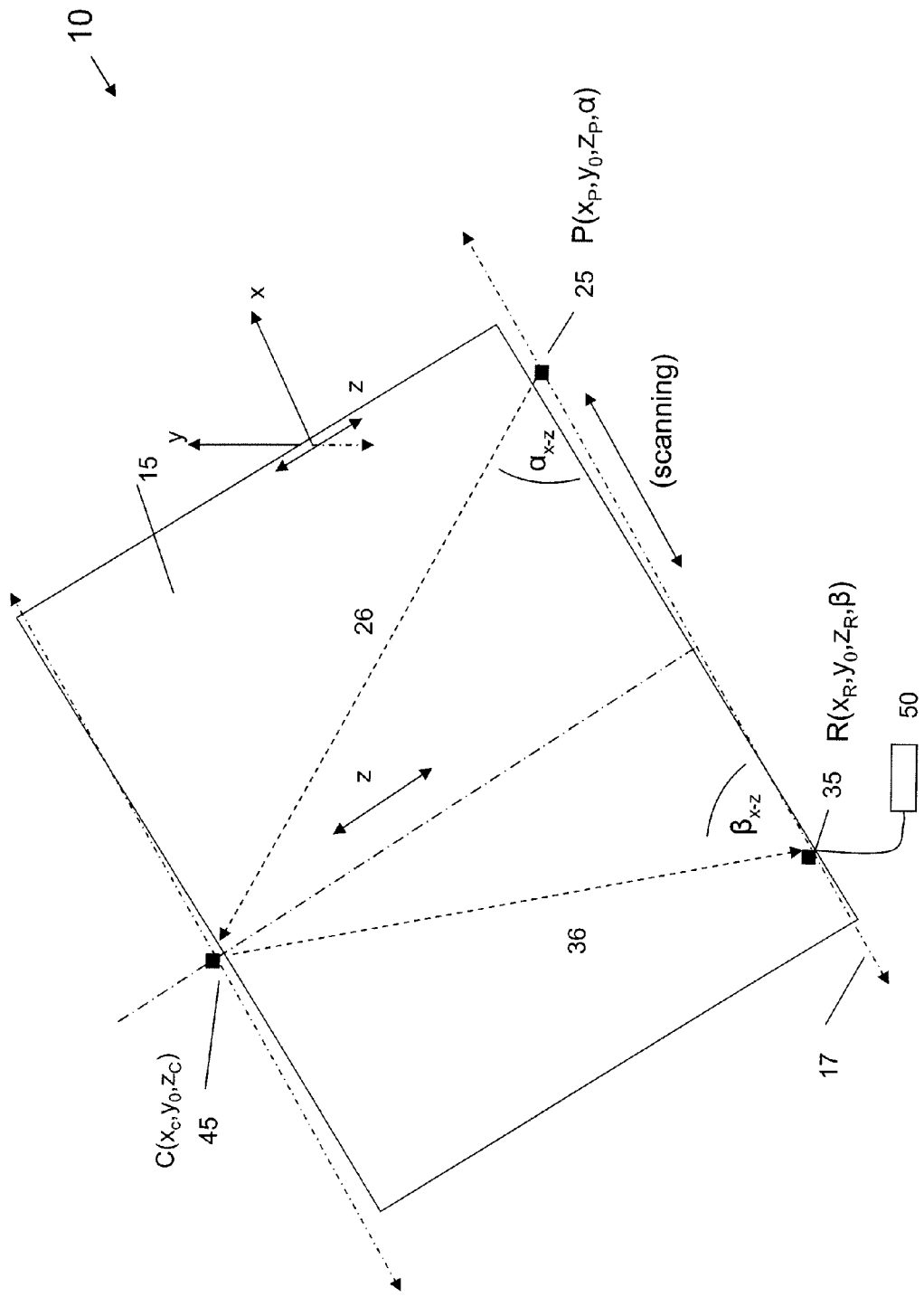
FIG. 1 is a schematic top plan view of a calibration system setup according to an embodiment of the invention.

An embodiment of the invention is directed to a slit plane image calibration system 10 as illustrated in FIG. 1. The calibration system is particularly suited to calibrating slit beam-based ophthalmic instruments such as anterior chamber analyzers from Bausch & Lomb Incorporated and Nidek Co., LTD, for example, or slit beam pachymeters (see, e.g., Snook U.S. Pat. No. 6,193,371). In these types of instruments, a slit beam is scanned across a subject's eye and a series of slit beam images is taken to obtain cross sectional viewing of the subject's cornea and to reconstruct corneal profiles, including an anterior surface profile, a posterior surface profile, and a corneal thickness profile. Thus embodiments according to the invention can be used to measure the slit beam profile and to determine the optical path of the slit beam at various scanning positions of the slit beam. The slit beam profile includes the slit beam width across the slit plane and the slit beam width variation along its propagation direction. The optical path includes the slit beam position, projection axis direction, and slit beam orientation with respect to the instrument axis and camera focal plane. Embodiments according to the invention are beneficial because the measurement accuracy and precision of a slit beam based optical pachymeter, for example, is highly dependent on the slit plane calibration.

Figure 6:
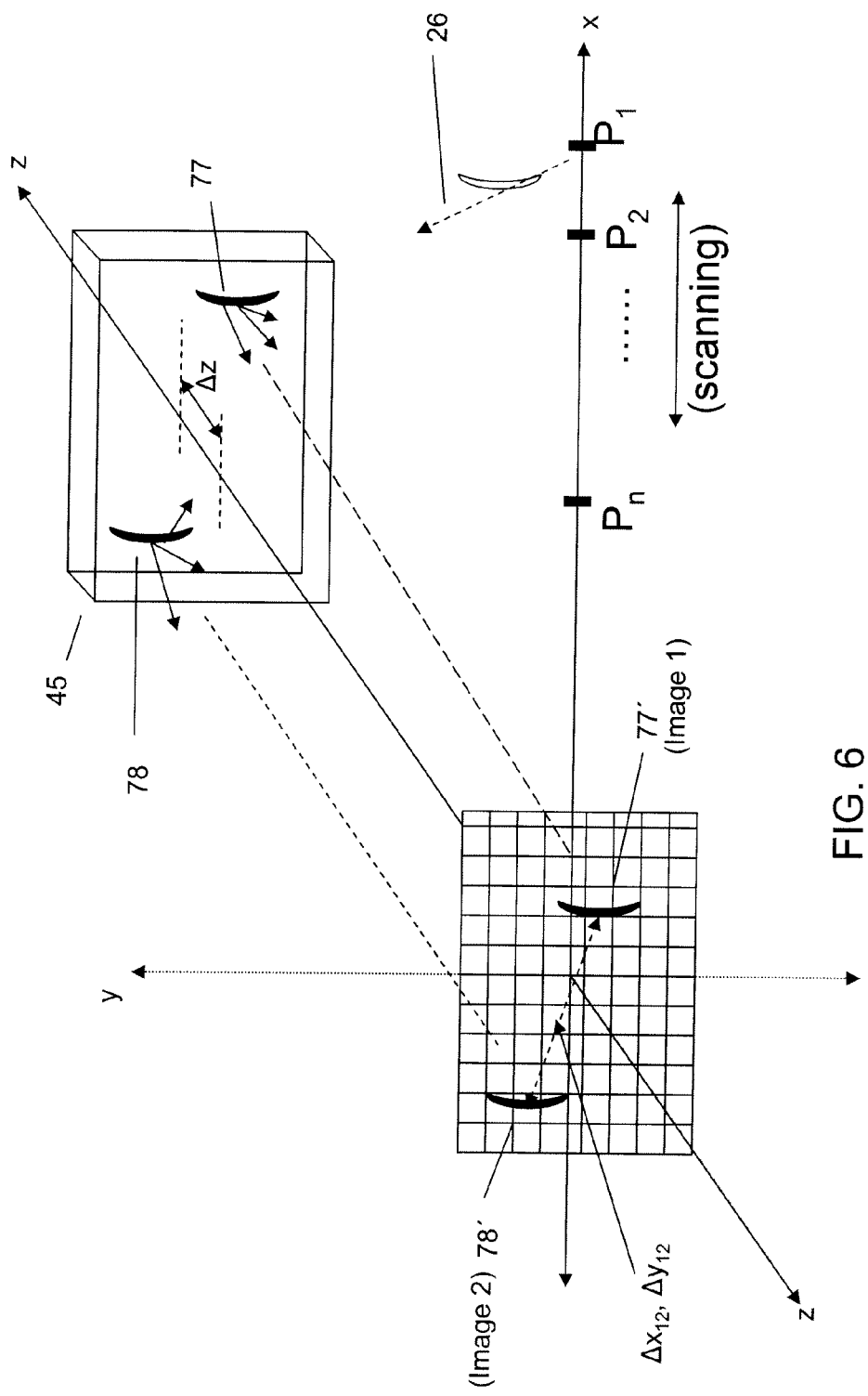
FIG. 6 is a schematic diagram illustrating a calibration indicia relationship according to an exemplary aspect of the invention.

The system 10 includes a slit illumination projector (P) 25 having an illumination projection axis 26 lying in the x-z plane 15 as shown. The projector is positioned at a selected reference location coordinate $(x_P, y_0, z_P)$ along a reference line 17. The projection axis 26 has a known direction (e.g., an angle defined in relation to a coordinate axis) in the plane relative to the reference line 17. The projector may be a Scheimpflug slit beam projector or other suitable incoherent illumination source known in the art. An illumination imager (R) 35 having an imaging axis 36 lying in the plane is positioned at a known imager location coordinate $(x_R, y_0, z_R)$ in the plane. A calibration component (C) 45 is located in the plane 15 at position coordinates $(x_C, y_0, z_C)$, where $z_C$ is measured perpendicular to the reference line 17, and $x_C$ is a position coordinate that locates the calibration component in the plane 15 spatially between the illumination projector and the illumination imager but not along the reference line 17. A computational processor 50 is shown operatively connected to the imager 35. The illumination projector and the imager can be moved relative to one another along imaginary reference line 17 as a means for scanning the illumination pattern across the calibration component surface, similar to the way the illumination pattern would be scanned across the subject's eye. Because the eye is a three-dimensional volume scatterer, it may be beneficial to translate the illumination pattern across the calibration surfaces to adjust for any nonlinearity between scan position and image edge and/or centroid detection. Reference is made to FIGS. 1 and 6, which illustrate exemplary scanning of the illumination pattern.

Figure 2:
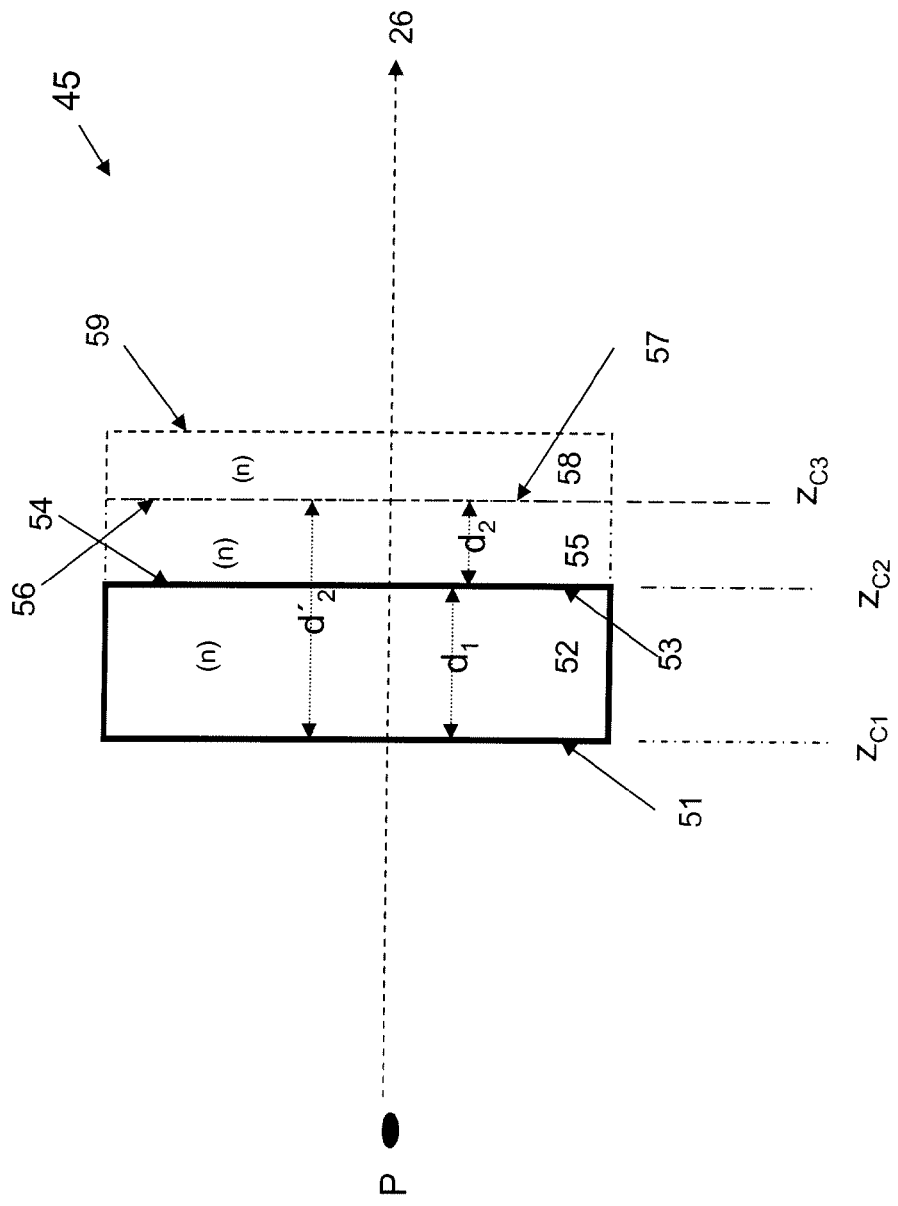
FIG. 2 is right side cross sectional view of a calibration component according to an exemplary aspect of the invention.
Figure 3:
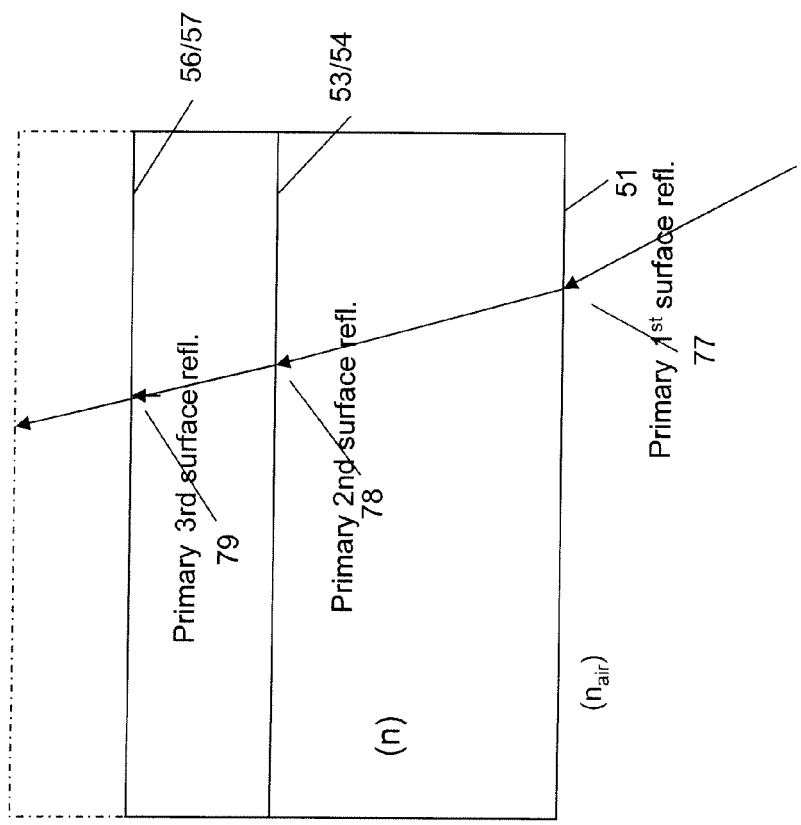
FIG. 3 is an illustrative top plan view of a calibration component according to an exemplary aspect of the invention.

The calibration component 45 includes at least a first optically transmitting and partially diffusely reflecting surface 51 disposed along the projection axis 26 at a known first surface location coordinate $(x_C, y_0, z_{C1})$ and a second optically transmitting and partially diffusely reflecting surface 53 disposed along the projection axis 26 at a known second surface location coordinate $(x_C, y_0, z_{C2})$ that is different than the first surface location coordinate. In a particular aspect, the calibration component 45 includes at least a third optically transmitting and partially diffusely reflecting surface 56 disposed along the projection axis 26 at a known third surface location coordinate $(x_C, y_0, z_{C3})$ that is different than the first and the second surface location coordinates. According to an exemplary aspect as illustrated in FIG. 2, the calibration component 45 comprises a plurality of stacked, optically transmitting plates 52, 55, . . . 58 . . . , each having a given thickness ($d_1$, $d_2$, . . . ). At least either a front surface (e.g., 51, 54, 57) or a back surface (e.g., 53, 56, 59) of each of the plates is a diffusely reflecting surface. Each of the plates is an optically transmissive material such as BK7 glass, for example, of index of refraction n. The first (i.e., as positioned along the projection axis 26 to receive illumination from P) plate 52 has an optically diffuse front surface 51 and a rear surface 53 that coincides with the optically diffuse front surface 54 of second plate 55. The surfaces 51 and 53/54 are parallely displaced a known, fixed distance $d_1$. Second plate 55 has a rear surface 56 that may be made optically diffuse. Alternatively, as shown by the dotted lines, calibration component 45 includes a third plate 58 having an optically diffuse front surface 57. The surfaces 53/54 and 56/57 are parallely displaced a known, fixed distance shown as $d_2$. The calibration component thickness from front surface 51 to surface 56/57 is shown as $d'_2$. In a particular aspect, $d_1$ is greater than $d_2$. This insures that secondary reflections from the multiple surfaces do not overlap or interfere with the primary diffusely reflected slit images 77, 78, 79 as illustrated in FIG. 3. Plate thicknesses may, alternatively, be equal.

Figure 4:
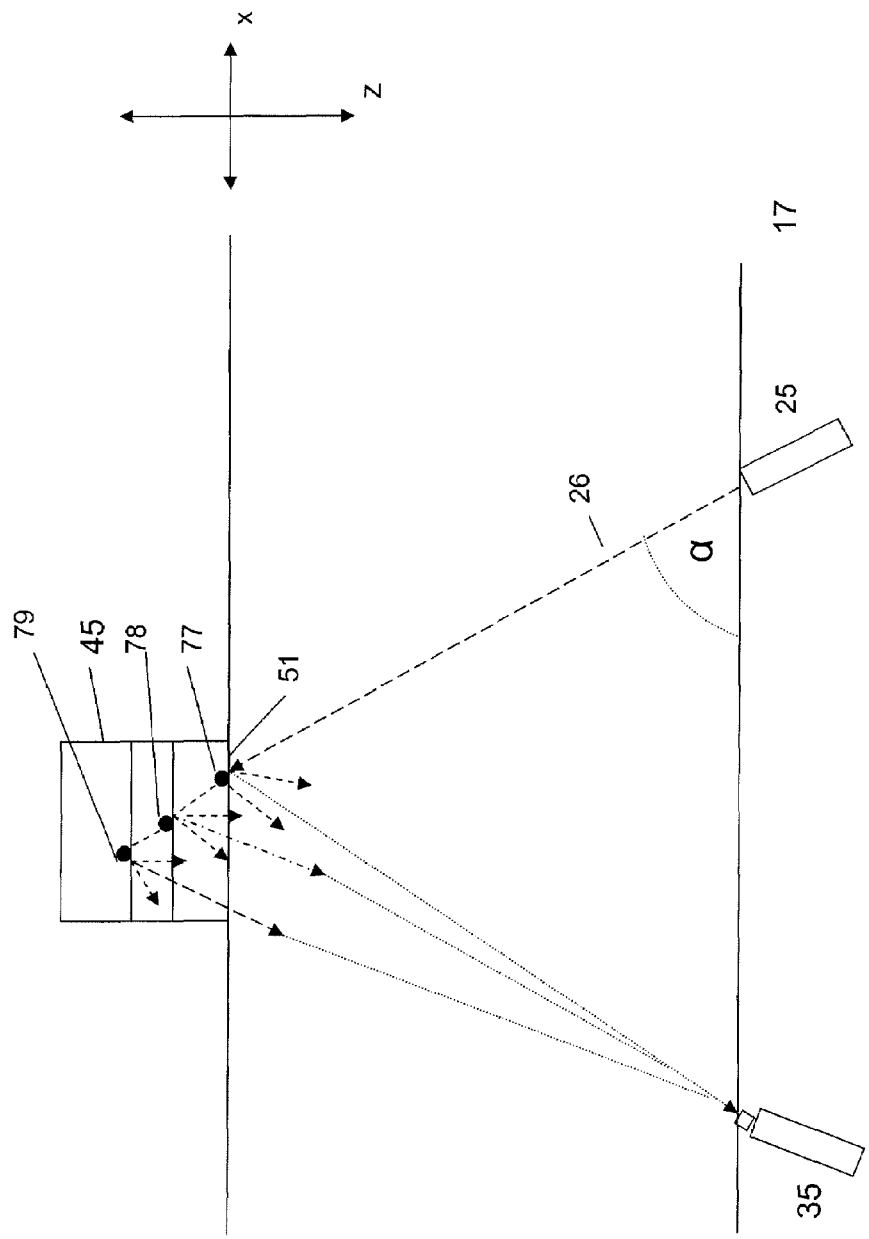
FIG. 4 is an illustrative top plan view of a calibration system according to an embodiment of the invention.

FIG. 4 shows an illustrative schematic in which the incident slit illumination axis 26 is incident on the first front surface 51 of the calibration component at an angle α (with respect to line 17), forming first diffusely scattered slit image 77 at distance coordinate $z_{C1}$. The light is refracted slightly as shown in FIG. 3 due to the index, n, of the plate 52. The second and third surface diffusely scattered slit images 78, 79 are shown displaced along the x-direction on respective surfaces 53/53 and 56/57 located at distance coordinates $z_{C2}$, $z_{C3}$. The angle α, while illustrated to be about 45 degrees, can be essentially any angle between 0 to 90 degrees such that the camera 35 can image the diffusely scattered slit illumination images from the surfaces of the calibration component 45. When the illumination pattern is scanned across the calibration component surface(s), the relative positions of the projector and the imager along reference line 17 will change while the angle α (i.e., the projection axis direction) remains, for the most part, the same.

Figure 5:
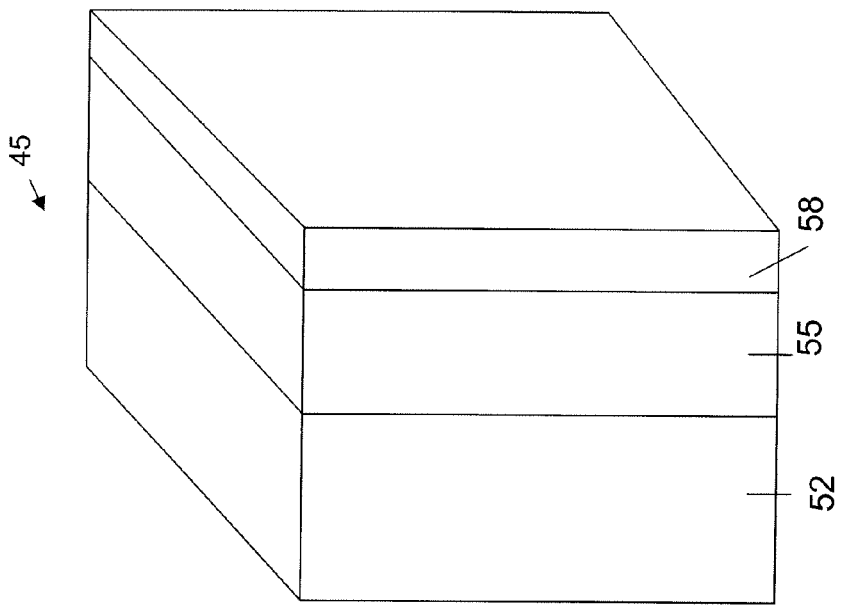
FIG. 5 is a perspective view of a calibration component according to an illustrative aspect of the invention.

FIG. 5 shows an illustrative perspective view of the calibration component 45. In this exemplary aspect, the calibration component consists of three stacked/fused glass plates 52, 55 and 58. Plate 52 includes an optically diffuse front surface that will be initially impinged by source illumination in the set-up as illustrated in FIG. 4. Plates 55 and 58 also have optically diffuse front surfaces whereupon the diffusely scattered illumination images are formed.

Based upon the position, orientation and separation coordinate parameters of the illumination projector, the calibration component surfaces, and the image sensor and the images formed thereon, the system processor can be programmed to determine a calibration indicia. In an exemplary aspect, the calibration indicia describes a relationship between a) the separation of corresponding coordinate parameters $\Delta x_{IMAGE\ 1,\ IMAGE\ 2}$, $\Delta y_{IMAGE\ 1,\ IMAGE\ 2}$ between at least two different diffuse illumination images on the sensor plane in the imager and, b) an axial separation distance $\Delta z_{C(n)}$ between at least two respective diffusely reflecting surfaces of the calibration component. This is diagrammatically illustrated in FIG. 6. Accordingly, once the system is so calibrated, the coordinates $\Delta x_{12}$, $\Delta y_{12}$ of the diffusely reflected slit images (e.g., image 1, image 2) from the diffusely scattering anterior and posterior surfaces of a subject's cornea formed on a flat camera sensor can be used to determine the depthwise (axial) separation $\Delta z_{C(n)}$, and thus the thickness, of the subject's cornea, for example. Stated differently, the $\Delta x$, $\Delta y$, and $\Delta z$ parameters are the projection of a corresponding section of the slit beam on the three coordinates. Calibration according to an embodiment of the invention allows the determination of camera measured $\Delta x$, $\Delta y$ values to a known $\Delta z$ at a known position of x, y, and z of the slit beam. This then provides a scale factor for the $\Delta x$ and $\Delta y$ values on the camera plane for a $\Delta z$ value of the slit beam. The scale factor is position dependent due to the vergence of the projected slit beam, the camera depth of focus, and because the slit beam angle varies slightly as it scans. Thus calibration is important to determine the scale factor between the $\Delta x$, $\Delta y$, and $\Delta z$ parameters as a function of the slit position.

Figures 7A, 7B:
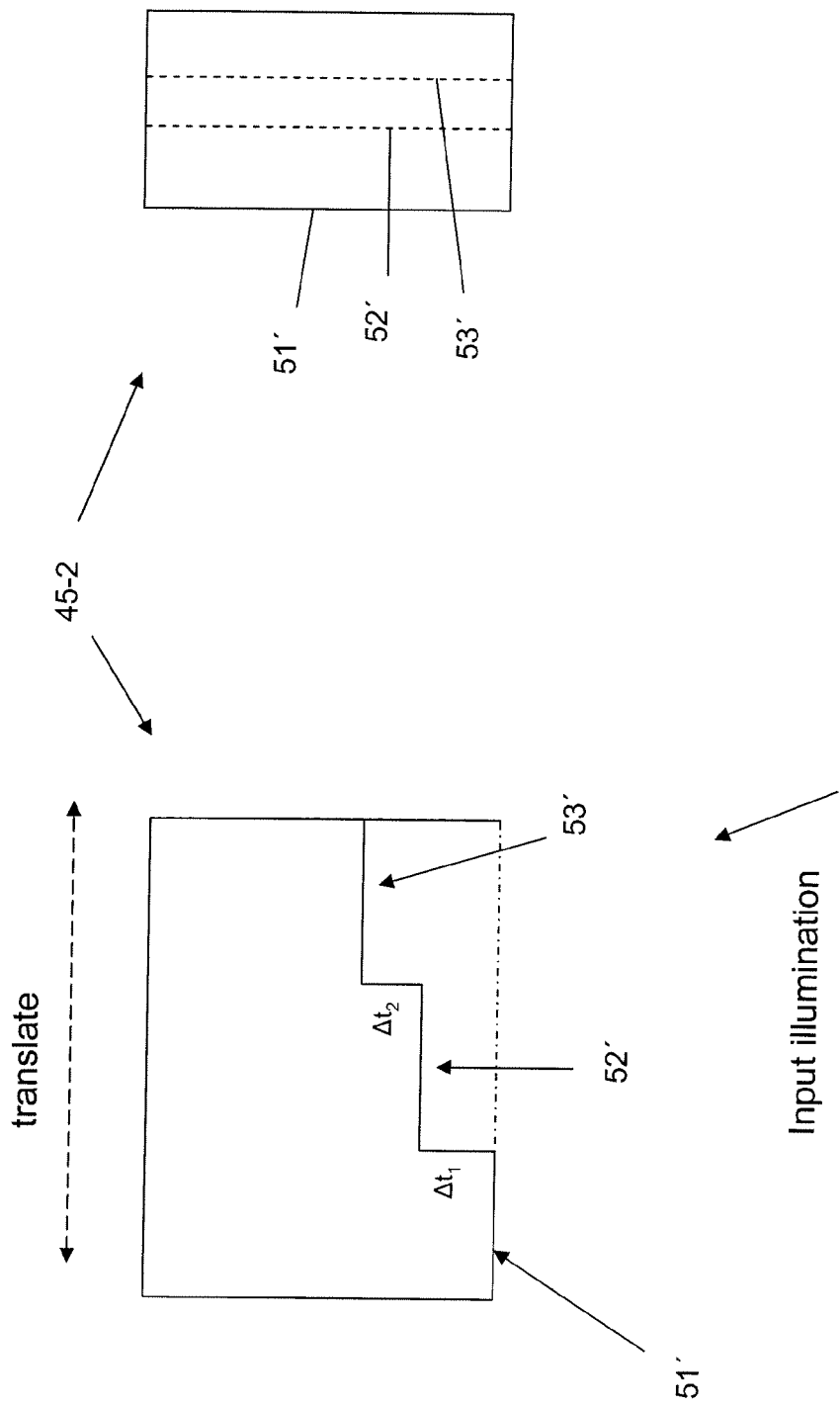
FIGS. 7A and 7B show a top plan view and a side elevational view, respectively, of a calibration component according to an alternative exemplary embodiment of the invention.

FIGS. 7A and 7B show a top plan view and a side elevational view, respectively, of a calibration component 45-2 according to an alternative embodiment of the invention. The exemplary component as illustrated has a first diffusely reflecting optical surface 51', a second diffusely reflecting optical surface 53' disposed parallel to surface 51' and displaced a known distance $\Delta t_{12}$ therefrom in a step-wise manner; and a third diffusely reflecting optical surface 56' disposed parallel to surfaces 51', 53' and displaced a known distance $\Delta t_{23}$ from surface 53' in a step-wise manner as shown. The component 45-2 may be translated in a direction parallel to the orientation of the diffusely reflecting surfaces to effect scanning of the slit beam illumination. Alternatively, the slit beam may be scanned as described above by moving the illumination projector.

Other alternative embodiments of a calibration component having different fixedly displaced, diffusely reflecting surfaces could include block-like or disc-like rotatable structures having a plurality of diffusely reflecting surfaces contained therein.

Figure 8:
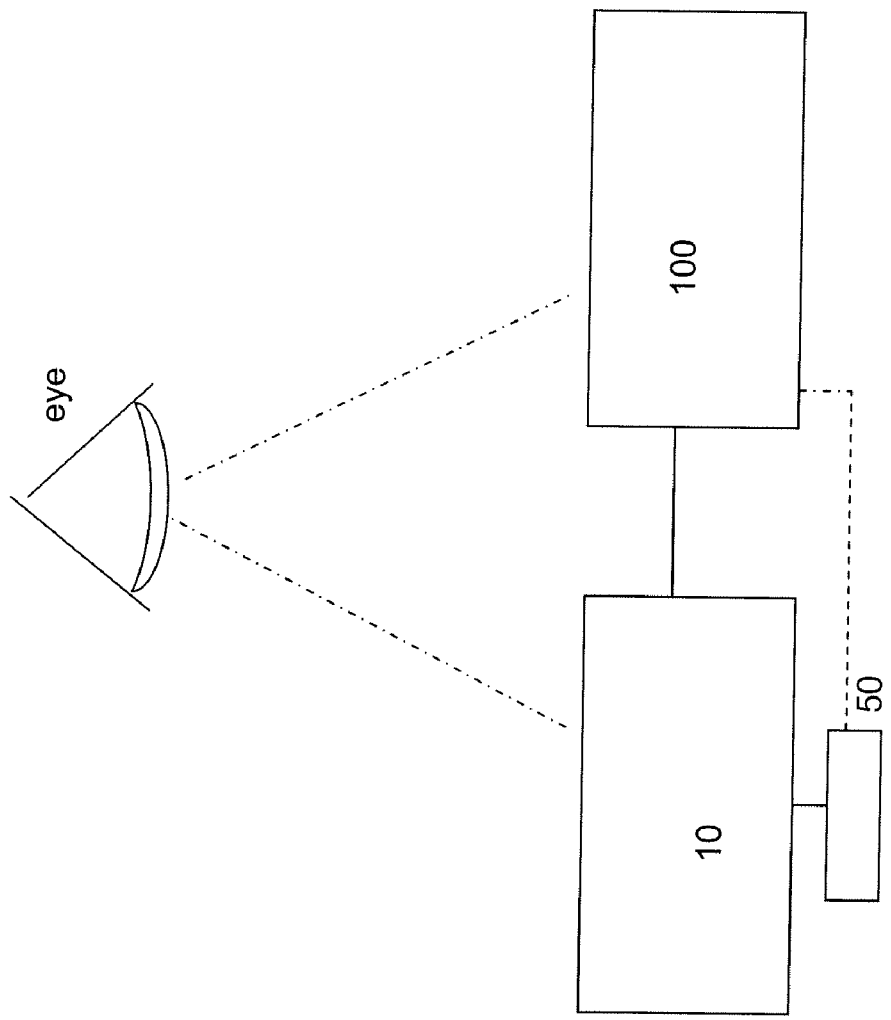
FIG. 8 is a schematic diagram of an exemplary system including a wavefront sensor according to an exemplary aspect of the invention.

According to an exemplary aspect of the invention as illustrated in FIG. 8, the calibration system 10 described herein may be utilized in conjunction with an ophthalmic wavefront sensor 100. The calibration system may suitably be a modifiable version of an eye topography system or an anterior corneal segment analyzer. An example of such a device is the Orbscan® IIIz ophthalmic analysis system. The combination of the calibration system 10, a wavefront sensor 100 and a processor 50 may form an integrated ophthalmic diagnostic calibration and measurement system.

The foregoing description of the preferred embodiments of the invention have been presented for the purposes of illustration and description. It is not intended to be exhaustive or to limit the invention to the precise forms disclosed. Many modifications and variations are possible in light of the above teachings. It is intended that the scope of the invention embodiments be limited not by this detailed description but rather by the claims appended hereto.

We claim:

1. An optical calibration system, comprising
   an illumination projector having an illumination projection axis lying in a plane, wherein the projector is positioned at a selected reference location coordinate ($x_P, y_0, z_P$) in the plane, further wherein the projection axis has a known projection axis direction in the plane;
   an illumination imager having an imaging axis lying in the plane, wherein the illumination imager is positioned at a known receiver location coordinate ($x_R, y_0, z_R$) in the plane;
   a calibration component comprising at least a first at least partially diffusely reflecting surface disposed along the projection axis at a known first surface location coordinate ($x_C, y_0, z_{C1}$) and a second at least partially diffusely reflecting surface disposed along the projection axis at a known second surface location coordinate ($x_C, y_0, z_{C2}$) that is different than the first surface location coordinate, the system configured such that the first at least partially diffusely reflecting surface and the second at least partially diffusely reflecting surface are disposed along the projection axis at a same time; and a processing component operatively coupled to the system and adapted to determine a spatial calibration indicia for the system.

2. The optical calibration system of claim 1, wherein the calibration component comprises at least a third at least partially diffusely reflecting surface disposed along the projection axis at a known third surface location coordinate that is different than the first and the second surface location coordinates.

3. The optical calibration system of claim 2, wherein the calibration component comprises a plurality of stacked, optically transmitting plates each having a given thickness, wherein at least one of a front and a back surface of each of the plurality of plates is an at least partially diffusely reflecting surface.

4. The optical calibration system of claim 2, wherein the calibration component comprises at least a first at least partially diffusely reflecting surface portion positionable in the path of the projection axis and a second at least partially diffusely reflecting surface portion disposed parallel to the first surface portion and displaced a known distance from the first surface.

5. The optical calibration system of claim 4, wherein the calibration component comprises at least a third at least partially diffusely reflecting surface portion disposed parallel to the first and second surface portions and displaced a known distance from at least one of the first and the second surface portions.

6. The optical calibration system of claim 3, wherein the given thicknesses of at least some of the plurality of plates are equal to one another.

7. The optical calibration system of claim 1, wherein the calibration component has a homogeneous index of refraction.

8. The optical calibration system of claim 3, wherein all of the plurality of plates have an equal index of refraction.

9. The optical calibration system of claim 1, wherein the at least first and second surfaces are flat.

10. The optical calibration system of claim 1, wherein the at least first and second surfaces are parallely displaced.

11. The optical calibration system of claim 1, each of the diffusing surfaces is at least one of an etched surface, a roughened surface, a coated surface, a frosted surface, and a ground surface.

12. The optical calibration system of claim 1, wherein the illumination projector produces a predetermined illumination pattern.

13. The optical calibration system of claim 12, wherein the illumination projector produces a slit light pattern.

14. The optical calibration system of claim 12, wherein the illumination projector is an incoherent light projector.

15. The optical calibration system of claim 1, wherein the calibration component is optical glass.

16. The optical calibration system of claim 1, wherein the illumination projector is a Scheimpflug slit beam projector.

17. The optical calibration system of claim 1, wherein the calibration indicia describes a relationship between a) the separation of corresponding coordinate parameters between at least two different diffuse illumination images on a sensor plane in the imager and, b) an axial separation distance between at least two respective diffusely reflecting surfaces of the calibration component.

18. A method for calibrating an optical system, comprising:
    projecting an illumination pattern from a selected projection location, having a projection axis and known projection axis direction;
    simultaneously illuminating a plurality of partially diffusing calibration component surfaces disposed in a path of the projection axis, each of said surfaces disposed at respective known calibration component surface locations along the projection axis that are different than one another;
    imaging the plurality of diffusely scattered illumination images from the plurality of optically diffusing calibration component surfaces on an image sensor positioned at a known imager location; and
    spatially calibrating the optical system based upon the projector, imager and calibration component surface locations, axis direction parameters, and sensor image parameters.

19. The method of claim 18, wherein the projecting step comprises projecting an incoherent illumination pattern.

20. The method of claim 19, wherein the projecting step comprises projecting a slit illumination pattern.

21. The method of claim 18, wherein calibrating the optical system comprises determining a relationship between a) the separation of corresponding coordinate parameters between at least two different diffuse illumination images on a sensor plane in the imager and, b) an axial separation distance between at least two respective diffusely reflecting surfaces of the calibration component.

22. An image calibration system, comprising:
    a slit illumination projector adapted to project a slit illumination pattern along an illumination axis;
    a calibration component having a plurality of diffusely reflecting surfaces, each of which is positioned along the illumination axis, each of which diffusely scatters at least a portion of the slit illumination pattern, the system configured such that the plurality of diffusely reflecting surfaces are disposed along the projection axis at a same time;
    a camera disposed so as to image each of the diffusely scattered slit patterns on each of the respective plurality of diffusely reflecting surfaces; and
    a processing component coupled to the camera and adapted to determine a spatial calibration indicia for the slit images.

23. The image calibration system of claim 22, wherein each of the slit illumination projector, the calibration component, and the camera have relative location and orientation coordinates sufficient for the processing component to determine the calibration indicia for the slit plane images.

24. The image calibration system of claim 22, wherein the slit illumination projector is adapted to project an incoherent slit illumination pattern.

25. The image calibration system of claim 24, wherein the slit illumination projector is a Scheimpflug slit beam projector.

26. The image calibration system of claim 22, wherein the calibration component has at least three diffusely reflecting surfaces.

27. The image calibration system of claim 22, wherein a separation distance between any two adjacent diffuse surfaces is different than a separation distance between any other two adjacent diffuse surfaces.

28. The image calibration system of claim 27, wherein the separation distance between a first diffuse surface and a second diffuse surface is greater than the distance between the second diffuse surface and a third diffuse surface.

29. The image calibration system of claim 22, wherein each of the plurality of diffusely reflecting surfaces are flat and mutually parallel.

30. The image calibration system of claim 22, wherein the calibration indicia describes a relationship between a) the separation of corresponding coordinate parameters between at least two different diffuse illumination images on a sensor plane in the imager and, b) an axial separation distance between at least two respective diffusely reflecting surfaces of the calibration component.

31. The image calibration system of claim 22, constituting a portion of a corneal topography analysis device.

32. The image calibration system of claim 31, further comprising an ophthalmic wavefront analyzer cooperatively engaged with the system.

33. The image calibration system of claim 22, constituting a portion of an anterior corneal segment analyzer device.

34. The image calibration system of claim 33, further comprising an ophthalmic wavefront analyzer cooperatively engaged with the system.

* * * * *